United States Patent [19]

Sheaks et al.

[11] 4,259,862
[45] Apr. 7, 1981

[54] SMOOTHNESS ABSORBENCY TESTER

[75] Inventors: Lloyd D. Sheaks; W. Howard Drew, both of Kalamazoo, Mich.

[73] Assignee: Kaltec Scientific Instrument, Inc., Kalamazoo, Mich.

[21] Appl. No.: 63,309

[22] Filed: Aug. 2, 1979

Related U.S. Application Data

[63] Continuation-in-part of Ser. No. 41,825, May 23, 1979, abandoned.

[51] Int. Cl.³ ............................................ G01N 7/04
[52] U.S. Cl. ...................................... 73/73; 118/407
[58] Field of Search ............................ 73/73; 118/407

[56] References Cited

U.S. PATENT DOCUMENTS

| | | | |
|---|---|---|---|
| 2,855,895 | 10/1958 | Burns et al. | 118/407 |
| 3,177,847 | 4/1965 | Schnierlein | 118/407 |
| 3,713,966 | 1/1973 | Lippke | 73/73 |
| 4,029,044 | 6/1977 | Hunter | 73/73 |
| 4,099,406 | 7/1978 | Fulkerson | 73/73 |

OTHER PUBLICATIONS

Publ. A New Apparatus ... Determine ... Roughness and Receptivity of Paper ... etc., by W. A. Wink, et al., TAPPI, vol. 40, No. 7, Jul. 1957, pp. 528-536.

Primary Examiner—Daniel M. Yasich
Attorney, Agent, or Firm—Blanchard, Flynn, Thiel, Boutell & Tanis

[57] ABSTRACT

A smoothness absorbency tester for testing the porosity characteristic of an elongated porous strip of material. A movable surface is provided on a frame and is adapted to support thereon the strip to be tested. A drive mechanism is provided for driving the movable surface. A blade is provided on the frame and is supported for movement toward and away from the movable surface. The blade defines an upwardly opening reservoir with one wall of the reservoir being defined by the aforesaid movable surface having the strip of material supported thereon. A liquid dispensing device is provided for dispensing a liquid of a predetermined viscosity into the reservoir so that the liquid contacts the strip of material. The blade means prevents a run-off of the liquid in the direction of movement of the strip of material and thereby holds the liquid in the reservoir to be absorbed by the strip of material moving relative to the blade. Structure is provided for detecting and indicating the absence of the liquid in the reservoir. Timing apparatus is provided for timing an interval of time between the introduction of liquid into the reservoir and the indication of the absence of liquid therein.

16 Claims, 13 Drawing Figures

SMOOTHNESS ABSORBENCY TESTER

CROSS REFERENCE TO RELATED APPLICATION

This application is a continuation-in-part of application Ser. No. 041,825, filed May 23, 1979, now abandoned.

FIELD OF THE INVENTION

This invention relates to a device for testing the smoothness and absorbency characteristic of an elongated and porous strip of material, such as paper.

BACKGROUND OF THE INVENTION

This invention arose out of a need to determine the smoothness and absorbency characteristic of paper. However, it is to be recognized that the features of this invention are readily applicable to the testing of the smoothness and absorbency characteristic of any type of porous material.

A problem has heretofore existed in the manufacture of paper, to one side of which is applied a silicone substance to enable the writing on the opposite side thereof to be transferred onto the upper surface of a separate second page without the use of a separate sheet of carbon paper. Often times this coated material will smear onto the upper surface of the second page. It was heretofore thought that the substance which was coated onto the paper was at fault and primarily responsible for the smearing characteristic. However, recent tests have indicated that the smearing characteristic is directly related to the smoothness and absorbency characteristic of the paper. It has now become a problem to determine which paper has suitable characteristics to enable this coating procedure to take place and to eliminate the smearing characteristic.

Accordingly, it is an object of this invention to provide a smoothness and absorbency apparatus to facilitate the determination of the porosity characteristic of a porous material prior to its being coated with a coating substance.

It is a further object of this invention to provide a method for determining the porosity characteristic of a porous material prior to its being coated with a coating material.

It is a further object of this invention to provide an apparatus which is durable, simple to operate, easy to maintain and to provide the necessary data from which it can be determined whether the tested material has a suitable porosity characteristic for the application of a specified coating material thereto.

It is a further object of this invention to provide an apparatus capable of driving an elongated strip of material at a specified speed relative to a reservoir from which is applied a liquid having a predetermined viscosity and a timer for timing the interval of time that it takes for the liquid to be absorbed into the moving strip of material.

SUMMARY OF THE INVENTION

In general, the objects and purposes of the invention are met by providing a smoothness absorbency tester for testing the porosity and smoothness characteristic of an elongated porous strip of material wherein a movable surface means is provided on a frame means and is driven relative to a blade means supported for movement toward and away from the surface means. The surface means is adapted to support the aforesaid strip of porous material. The blade means and the surface means are urged into engagement with each other with a predefined amount of force to define an upwardly opening reservoir. The strip of material is driven with the movable surface means beneath the blade means. Liquid dispensing means are provided for dispensing a predefined amount of liquid of a predetermined viscosity into the reservoir so that the liquid contacts the strip of material. The blade means prevents a run off of the liquid in the direction of movement of the strip of material and thereby holds the liquid in the reservoir to be absorbed by the strip of material. A detecting and indicating device is provided for detecting and indicating the absence of a liquid in the reservoir. Timing means is provided for timing an interval of time between the introduction of liquid into the reservoir and the indication of the absence of liquid therein.

Further objects and purposes of this invention will be apparent to persons acquainted with apparatus of this general type upon reading the following specification and inspecting the accompanying drawings.

DETAILED DESCRIPTION

Figure 1:
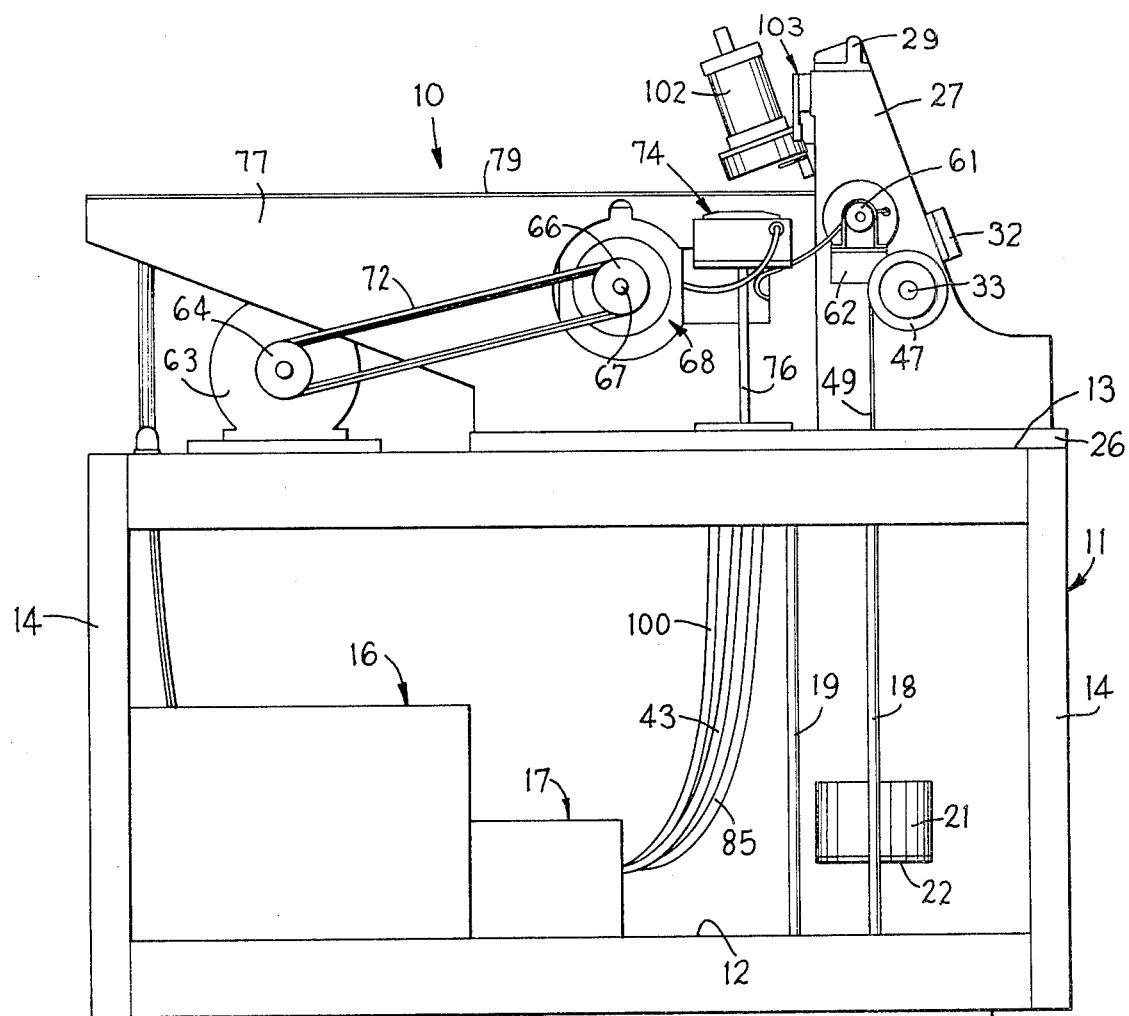
FIG. 1 is a side elevational view of a smoothness absorbency tester embodying the invention.

Certain terminology will be used in the following description for convenience in reference only and will not be limiting. The words "up", "down", "right" and "left" will designate directions in the drawings to which reference is made. The words "in" and "out" will refer to directions toward and away from, respectively, the geometric center of the device and designated parts thereof. Such terminology will include the words above specifically mentioned, derivatives thereof and words of similar import.

The smoothness absorbency tester 10 includes a frame 11 having a pair of vertically spaced and horizontally aligned mounting surfaces 12 and 13. The mounting surfaces 12 and 13 are each secured to plural upright and parallel legs 14. An air compressor and drive motor therefor are mounted on the mounting surface 12 and are housed in a housing 16. The air compressor has an air outlet which is connected to an accumulator tank housed within a housing 17 on the mounting surface 12. The accumulator tank has plural outlet nozzles therefrom to each of which is attached regulator valves so that the air pressure to the various components on the tester can be accurately regulated. The various components requiring air pressure to be supplied thereto will be described in more detail below. Since the air compressor and accumulator tank are known elements, they are not shown in any detail in the drawings. In addition, and if desired, the air compressor can be omitted in those instances where the user has its own air supply. In this instance, the air supply will be connected to the accumulator tank.

Figure 3:
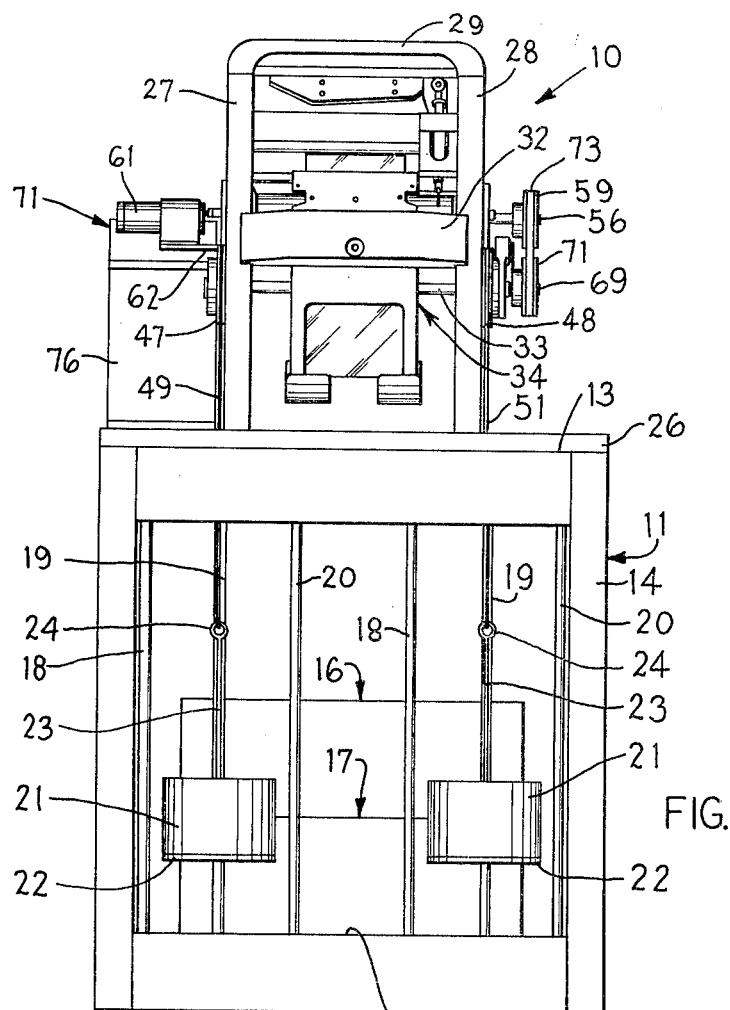
FIG. 3 is an end view of the apparatus as viewed from the right end appearing in FIG. 1.

Two sets of plural upright guide bars 18, 19 and 20 (FIG. 3) are secured to and extend between the mounting surfaces 12 and 13. The guide bars 18, 19 and 20 define a trianglelike arrangement and each set serves to guide a vertically elevatable weight 21 therebetween. The weight 21 is composed of plural weight segments each having a predefined weight so that the magnitude of the weight can be accurately controlled. The plural weight segments are mounted onto a platform 22 to which is secured and extends upwardly therefrom a support rod 23 having an eyelet 24 at the upper end thereof.

A mounting plate 26 (FIG. 2) is mounted on the mounting surface 13. A pair of laterally spaced side plates 27 and 28 are secured to and extend upwardly from the mounting plate 26. A cross member 29 (FIG. 2) is secured to and extends between the upper ends of the side plates 27 and 28. In addition, other crosswise extending members 31 and 32 are secured to and extend between the side plates 27 and 28 to provide added rigidity for the frame defined by the aforesaid side plates.

A shaft 33 (FIG. 1) extends between and is rotatably supported on bearing members mounted on the side plates 27 and 28. A mounting bracket 34 is fixedly secured to the shaft 33 and is movable therewith. The mounting bracket 34 has a flat surface 36 and a shelflike member 37 having an upwardly facing surface. A flat glass plate 38 or other suitable flat platelike material, as steel, is mounted on the upwardly facing surface of the shelflike member 37 and rests against the flat surface 36 on the mounting bracket 34. The flat plate 38 has a flat surface 38A thereon, the flatness of which is very precisely controlled. Appropriate guides 40 (FIG. 6) are provided on the mounting bracket 34 for holding the lateral edges of the flat plate 38 fixedly oriented with respect to the mounting bracket 34. If desired, a spring detent member 39 can be provided on the cross member 32 to urge the flat plate 38 into tight engagement with the guides 40. This structure will prevent the flat plate from moving relative to the mounting bracket 34 during operation.

A roller 41 (FIG. 6) of suitable material is rotatably secured to the mounting bracket 34 and is movable therewith. The peripheral surface of the roller 41 is precisely machined so that it is cylindrical and engages one side of the flat plate 38 evenly across the width thereof.

An air supply manifold 42 (FIG. 6) is provided on the mounting bracket 34 and extends crosswise thereof. Air is supplied to the manifold 42 through a conduit 43. The conduit 43 is connected in fluid circuit with one of the air regulator valves on the accumulator tank in the housing 13. In this embodiment, the air regulator valve is adjusted to five psi. A pair of air jet nozzles 44 and 46 extends around the opposite lateral edges of the flat plate 38. The outlet from each of the nozzles 44 and 46 is very precisely located and this location will be explained in more detail below.

Figure 6:
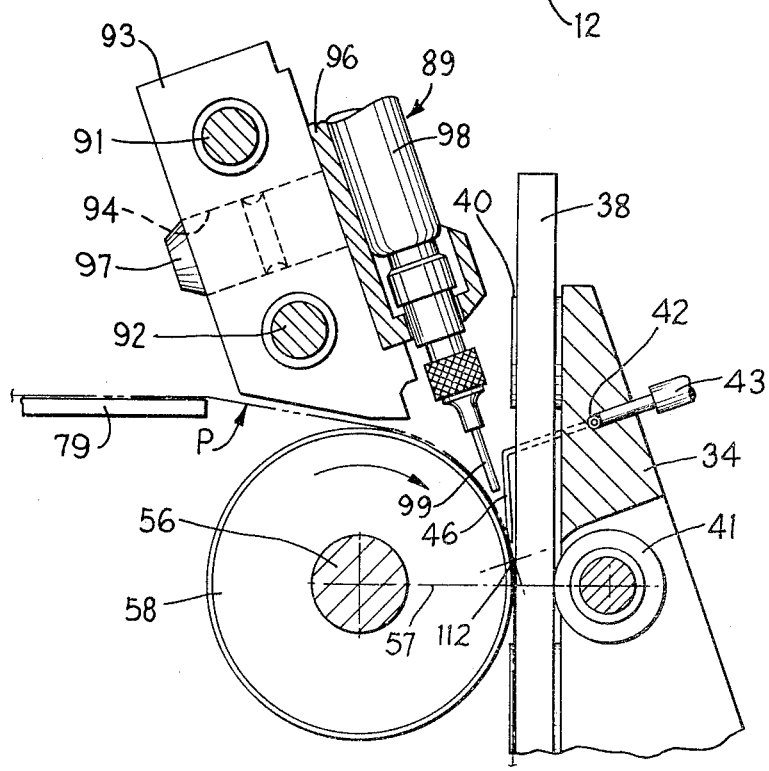
FIG. 6 is an enlarged fragmentary illustration of a portion of FIG. 4.
Figure 4:
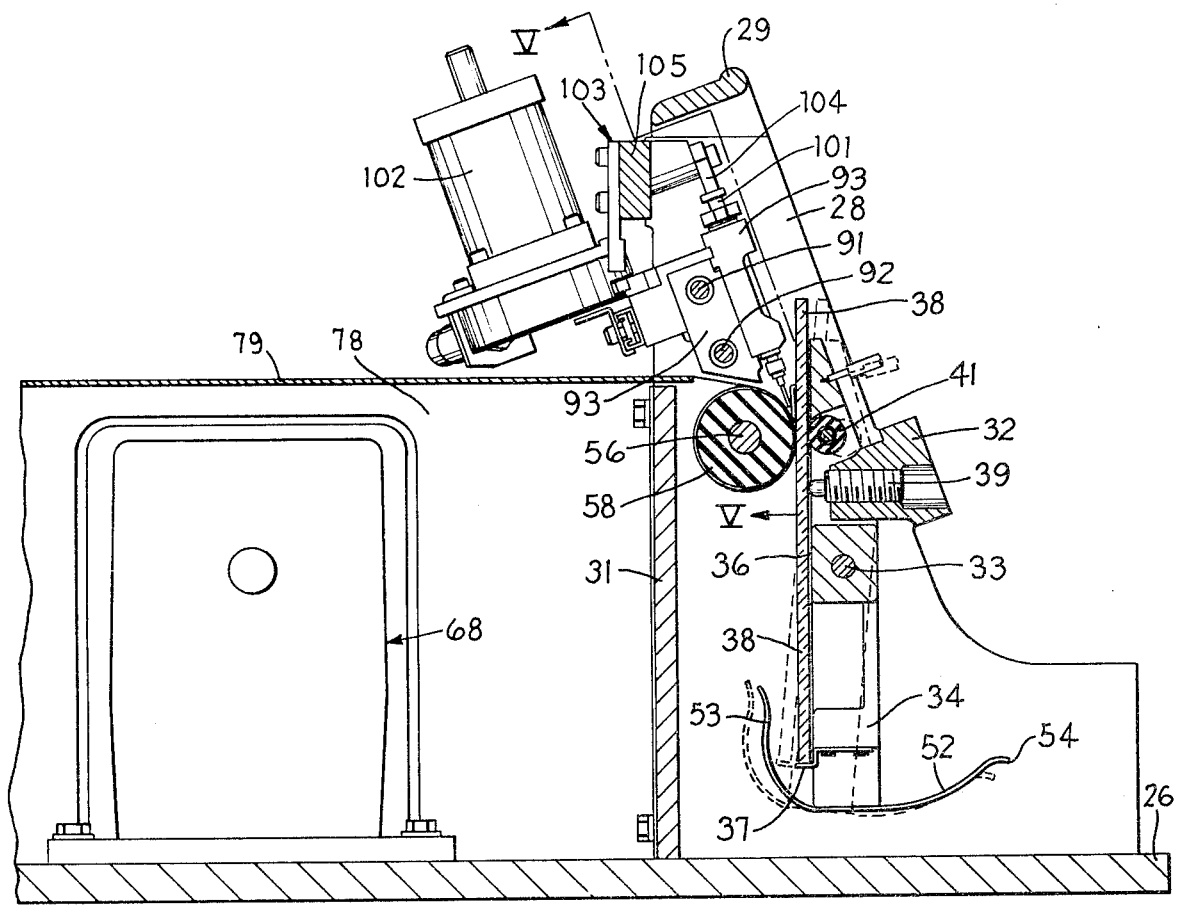
FIG. 4 is a central sectional view taken through a fragment of the apparatus, particularly along the line IV—IV in FIG. 2.

The shaft 33 has a pair of pulleys 47 and 48 (FIG. 3) secured thereto and rotatable therewith. The pulleys 47 and 48 are each located on the outside of the side plates 27 and 28, respectively. A cable 49 is secured to the pulley 47 at one location on its periphery, extends around the perimeter of the pulley and down through openings in the mounting plate 26 and mounting surface 13 and is attached at its lower end to the eyelet 24 on the upper end of one of the weight carrying support rods 23. Similarly, a cable 51 is secured to the pulley 48 at one location on its periphery, extends around the perimeter of the pulley and down through openings in the mounting plate 26 and mounting surface 13 and is attached at its lowermost end to the eyelet of a second weight carrying support rod 23. The platforms 22 for the pair of weight carrying support structures are elevated above the mounting surface 12. As a result, a torque is applied to the shaft 33 to effect an urging of the mounting bracket 34 and glass plate in a counterclockwise direction (FIGS. 4 and 6).

The mounting bracket 34 (FIG. 3) has a strip receiving tray 52 secured thereto below the shaft 33. The leading edge or left edge 53 (FIG. 4) of the receiving tray 52 is spaced from the side of the flat plate 38 which is remote from the shaft 33. The trailing edge or right edge 54 of the receiving tray 52 is located on the opposite side of the flat plate 38 from the leading edge thereof and preferably spaced from the mounting bracket 34 to provide easy access thereto between the side plates 27 and 28.

A further shaft 56 (FIG. 6) is rotatably mounted on and extends between the side plates 27 and 28. The location of the axis of rotation of the shaft 56 is preferably in a horizontal plane containing the axis of rotation of the roller 41. This plane is indicated by the reference numeral 57 in FIG. 6. A cylindrical roller 58 precisely machined to a specified diameter throughout the entirety of its length is secured to the shaft 56 and is rotatable therewith in the direction of the arrow illustrated in FIG. 6. The material of the roller is of a hard rubber material having an elastic deformation characteristic which will undergo a maximum of 0.003 inches of deformation in response to an applied force by the flat plate 38 of forty-six pounds, that is, twenty-three pounds on each of the platforms 22. The reason for this will be explained below. The exterior surface of the roller 58 is to engage the flat plate 38 even over the width thereof. This will be discussed below in more detail. One end of the shaft 56 (right end in FIG. 5) has a pulley 59 fixedly secured thereto. The opposite end of the shaft 56 is operatively connected to a tachometer device 61 for measuring the number of revolutions per minute that the shaft 56 is rotating. The tachometer device has a meter (not illustrated) for displaying the output thereof. The tachometer device 61 is supported on a bracket 62 fixedly secured to the external surface of the side plate 27. A drive motor 63 is fixedly secured to the mounting surface 13 on the frame 11. The output shaft of the motor has a pulley 64 (FIG. 2) thereon which is radially aligned with a pulley 66 on an input shaft 67 to a variable speed output control member 68.

The output shaft 69 of the variable speed control device 68 has a pulley 71 thereon which is radially aligned with the pulley 59. A belt 72 interconnects the pulleys 64 and 66 and a belt 73 interconnects the pulleys 59 and 71. The variable speed control device 68 is manually controlled by a control member 74 mounted on a support bracket 76 secured to the upper surface of the mounting plate 26.

A pair of side plates 77 and 78 extends to the left (FIG. 1) from the side plates 27 and 28, respectively. The side plates 77 and 78 are each secured to the upper surface of the mounting plate 26. A support plate 79 is secured to and extends between the upper edges of the side plates 77 and 78. The upper surface of the support plate 79 is positioned slightly above the uppermost part of the peripheral surface of the cylindrical roller 58 (FIG. 6) and the rightmost edge thereof terminates proximate the exterior surface of the roller 58, as illustrated in FIG. 6.

The aforesaid description of the cylindrical roller 58 and the support therefor combined with the weight 21 forcing the roller 41 to urge the flat plate 38 counterclockwise effects an urging of the flat plate 38 into engagement with the peripheral surface of the roller 58 along a line that is contained within the plane 57. As a result, the flat plate 38 defines a bladelike device, the purpose of which will be set forth below in more detail. The outlet for each of the nozzles 44 and 46 is spaced above this line of engagement. As a result, the peripheral surface of the roller 58 and the external surface of the bladelike flat plate 38 define an upwardly opening V-like shaped reservoir bounded on the lateral sides by the nozzles 44 and 46. The purpose of this construction will be explained below.

Figure 7:
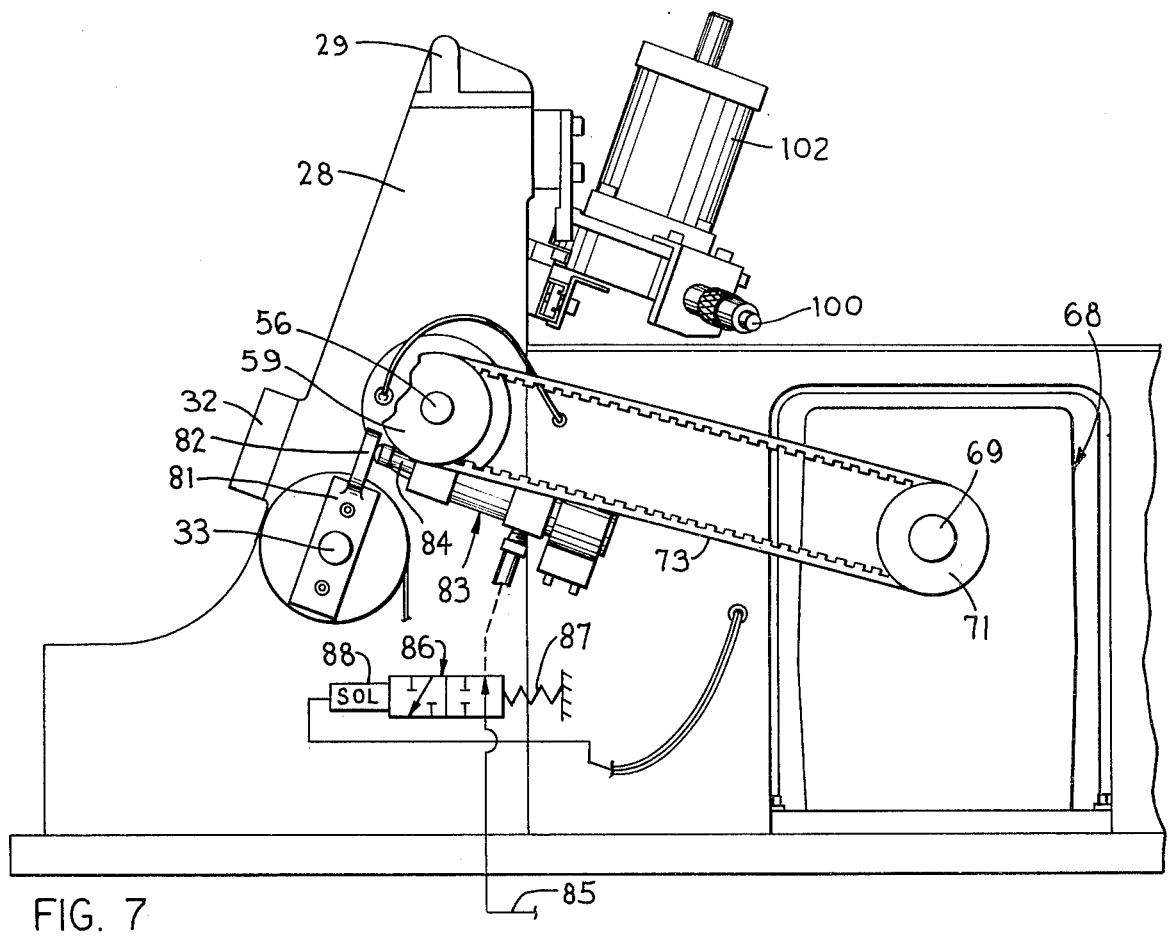
FIG. 7 is a side view of a fragment of the apparatus viewed from the opposite side of FIG. 1.

The normal position of the flat plate 38 is in engagement with the roller 58. When it is desired to move the flat plate 38 away from the peripheral surface of the roller 58, the appropriate structure for doing so is illustrated in FIG. 7. More specifically, a lever arm 81 is fixedly secured to the shaft 33, which lever arm has a flange 82 thereon. An air operated power cylinder 83 is fixedly secured to the side plate 28 and has a piston rod 84 which engages the flange 82. In this particular embodiment, the power cylinder 83 is positively driven in one direction to effect a movement of the piston rod 84 leftwardly and is retracted by a spring not illustrated. If desired, the power cylinder 83 could be a double-acting cylinder driven positively in both directions by fluid pressure. Air pressure at about twenty-five psi is supplied from the pressure regulator valve on the accumulator tank to the power cylinder 83 through a conduit 85 and a valve 86 biassed to the left by a spring 87 and positively shifted to the right by a solenoid 88. When the solenoid 88 is deactivated, the spring 87 will urge the valve to the position shown to supply air pressure to the power cylinder 83 to effect a driving of the piston rod 84 leftwardly to move the lever arm 81 counterclockwise to effect a driving of the flat plate 38 away from the peripheral surface of the roller 58. It will, of course, be recognized by those skilled in the art that if the power cylinder 83 is driven in both directions, namely, is a double-acting cylinder, the valve 86 will be modified to effect a fluid supply to alternate ends of the power cylinder.

A liquid dispensing apparatus 89 (FIG. 6) is mounted on and is generally positioned between the side plates 27 and 28. A pair of guide rails 91 and 92 is secured to and extends between the side plates 27 and 28. A carriage 93 is slidably mounted on the guide rails 91 and 92 and is adapted to move between the side plates 27 and 28. The carriage 93 has an opening 94 therein. A removable container holding member 96 has a pin 97 extending away from one side thereof and is adapted to be received into the opening 94 in the carriage 93. The tolerance between the outer diameter of the pin 97 and the inner diameter of the opening 94 is such as to effect a snug holding of the container holding member 96 on the carriage 93. Additional detent mechanisms (not illustrated) serve to prevent axial movement of the pin 97 relative to the carriage 93. A liquid holding container 98 is received in the container holding member 96, which container has an outlet opening in the form of an elongated nozzle 99 projecting into the V-like shaped reservoir defined by the peripheral surface of the roller 58 and the adjacent surface of the flat plate 38. In this particular embodiment, the container 98 has a cylindrical body and slidingly receives a reciprocal plunger 101 in the upper end thereof. As a result, the container holding member 96 can be removed from the carriage 93 and carried to a location permitting a filling of the container 98 with a liquid having a predetermined viscosity. Once the liquid is in the container 98, the plunger 101 will be inserted and will have a position extending upwardly from the body of the container 98.

An air operated rotary drive mechanism 102 (FIG. 4) is secured to the side plates 27 and 28 by any convenient type of mounting structure 103. This particular drive unit 102 produces a rotary output which effects a linear reciprocation of a rack (not illustrated) secured to the carriage 93. The details of this particular drive are well known in the art and are not, therefore, illustrated in detail. The drive unit 102 has a pair of solenoids 121 and 125 (see FIG. 8) thereon to effect rotation in opposite directions to cause the rack to be moved linearly in opposite directions between the side plates 27 and 28. This movement will cause the carriage 93 to move between the side plates 27 and 28. Air pressure of about forty psi is supplied from a pressure regulator valve on the accumulator tank through a conduit 100 (FIGS. 1 and 7) to the drive unit 102.

A cam 104 (FIG. 5) is pivotally secured to a cross member 105 secured to and extending between the side plates 27 and 28. The cam 104 has a cam surface 106 thereon. The angle of the cam surface 106 can be adjusted to an angle of between 0° and 25° relative to the longitudinal axes of the guide rails 91 and 92. To facilitate this adjustment, an elongated slot 107 is provided in the end of the cam 104 remote from the pivot axle 108 therefor and receives an externally threaded stud therein. A knurled knob 109 is threadedly engaged with the stud to facilitate a tightening of the cam 104 in the desired position. A placement of the container holding member 96 having a filled container 98 therein onto the carriage 93 will cause the plunger 101 to engage the cam surface 106 when the carriage 93 is moved from its rightmost position (illustrated in broken lines in FIG. 5) to its leftmost position illustrated in solid lines in FIG. 5. The plunger 101 will be urged into the container 98 to dispense the liquid therein out through the nozzle 99.

Figure 2:
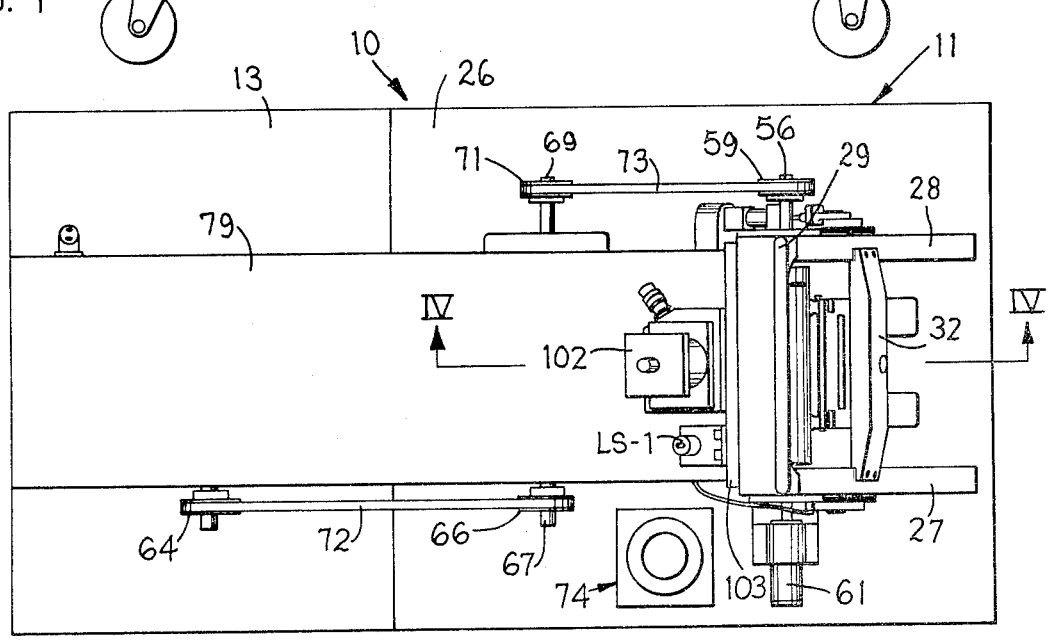
FIG. 2 is a top view thereof.

A proximity switch LS-1 (FIGS. 2 and 8) is mounted on the mounting structure 103 as illustrated in FIG. 2. The proximity switch LS-1 is normally open and will become closed in response to the carriage 93 being located adjacent thereto.

Figure 5:
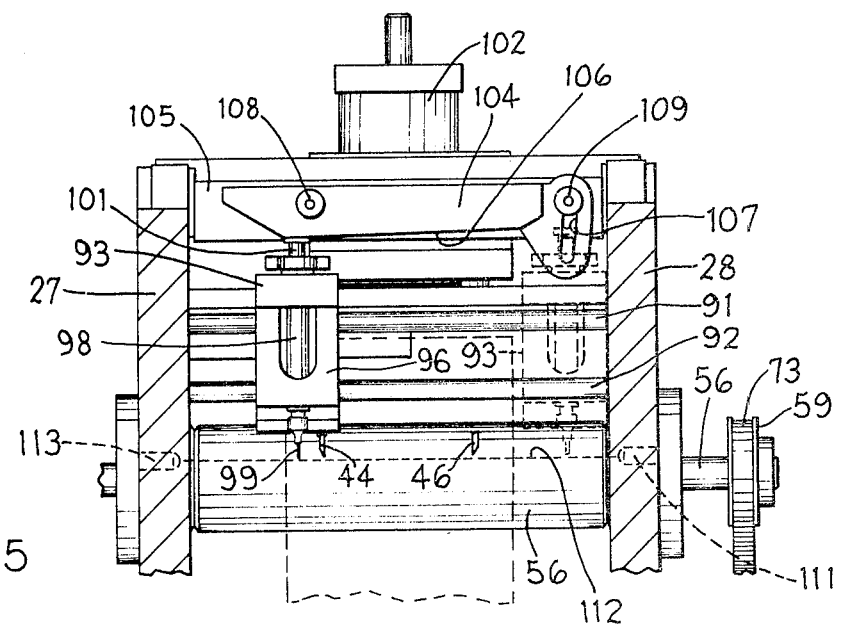
FIG. 5 is a view taken along the line V—V in FIG. 4.

A light source 111 (FIG. 5) is mounted in the side plate 28 and generates a path of light generally following the broken line 112 illustrated in FIG. 5. A phototube 113 is mounted in the side plate 27 and is adapted to detect the light emitted by the light source 111 along the path 112. The location of the path of light 112 is spaced slightly above the plane 57 (FIG. 6) and generally is located at the very bottom of the reservoir defined by the outer surface of the roller 58 and the flat plate 38. In other words, the path of light 112 would be located just slightly above the bottom of the V-like reservoir and below the outlet openings for the air supplying nozzles 44 and 46.

Figure 8:
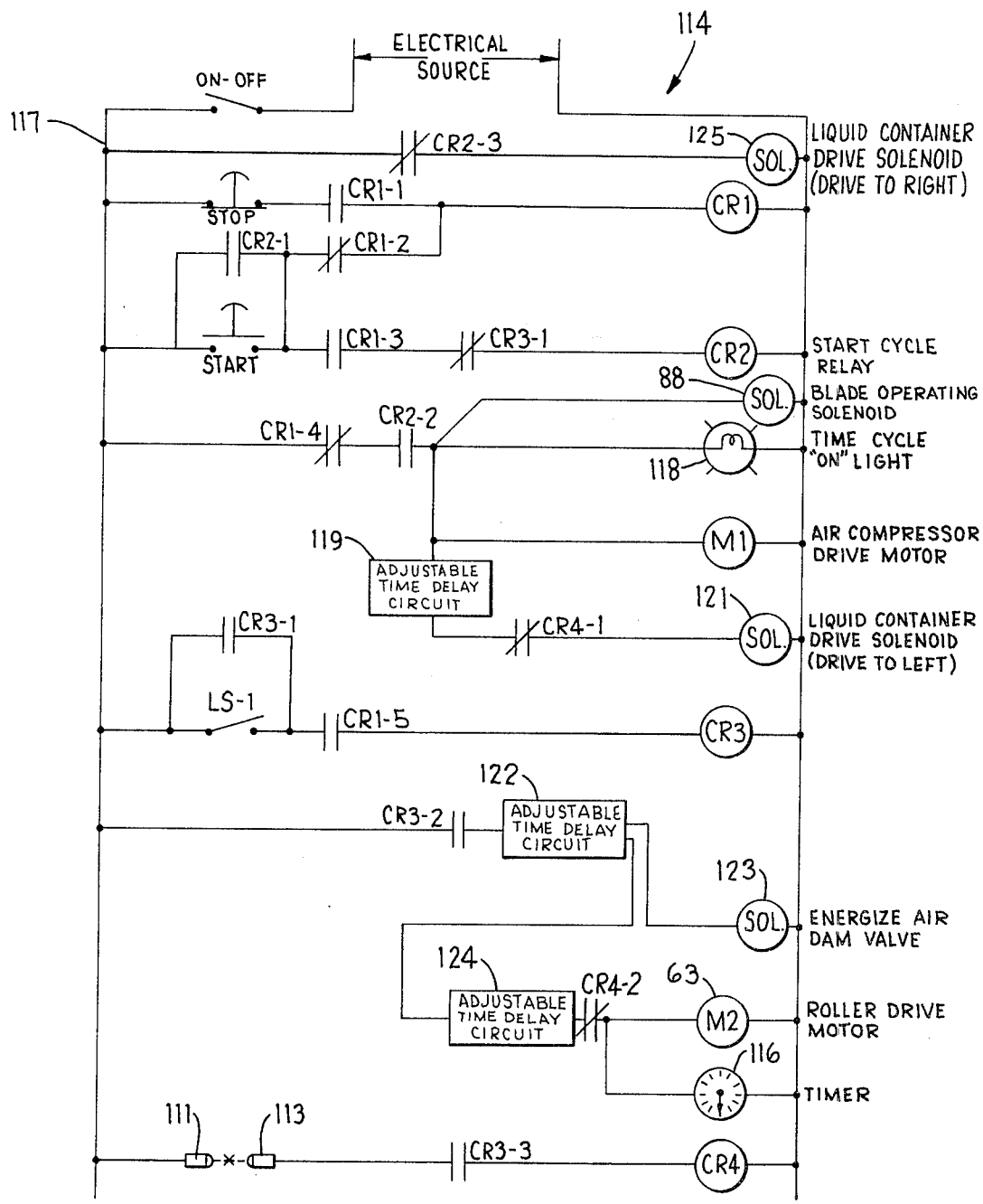
FIG. 8 is an electrical circuit diagram for the apparatus.

FIG. 8 illustrates an electrical circuit 114 which is positioned between the side plates 77 and 78 and beneath the support plate 79. The electrical circuit 114 includes an electrical timer 116, the position of which is located for easy viewing on the tester 10, such as on the uppermost surface of the mounting plate 26 adjacent the right end (FIG. 1) thereof. The actual mounting of the timer 116 is not illustrated in FIGS. 1 to 7. However, it is to be understood that the timer can be mounted utilizing any convenient form of structure. In addition, the ON-OFF, STOP and START switches are not shown in FIGS. 1 to 7. These switches can be located at any convenient location on the frame 11 and the precise location thereof is not critical to the invention and have, therefore, not been illustrated.

The electrical control circuit 114 is connected to any convenient type of electrical source and electrical power to the line 117 is controlled by an ON-OFF switch. Each of the control relays has several contacts associated therewith. For example, the control relay CR1 has five sets of contacts CR1-1 through CR1-5. The control relay CR2 has two sets of contacts CR2-1 and CR2-2. The control relay CR3 has three sets of contacts CR3-1 to CR3-3. The control relay CR4 has two sets of contacts CR4-1 and CR4-2. An effort has been made to place all of the contacts for the various relays in a vertically aligned relation. There has been an exception, however, and this appears with respect to the contact CR2-1 for the control relay CR2, the contact CR3-1 for the control relay CR3 and the contact CR4-2 for the control relay CR4.

Further, the contacts CR1-1, CR1-3, CR1-4 and CR1-5 are normally open contacts, whereas the contact CR1-2 is normally closed. Both of the contacts for the control relay CR2 are normally open contacts. The contacts CR3-1, CR3-2 and CR3-3 are normally open contacts. The contacts CR4-1 and CR4-2 are normally closed contacts.

It will be readily understood from the electrical schematic diagram appearing in FIG. 8 as to how each of the switches and control relays are connected into the circuit and further discussion of this circuit appears to be unnecessary.

OPERATION

Although the operation of the device embodying the invention has been indicated somewhat above, the operation will be described in detail hereinbelow for the purpose of convenience.

When it is desired to test the porosity and smoothness of an elongated strip of material, such as paper, a paper strip P (FIG. 6) is placed on the support surface 79 and between the flat plate 38 and the peripheral surface of the roller 58. The ON-OFF switch is turned on to promptly energize the solenoid 125 to effect a movement of the carriage 93 to its rightmost position. The container 98 is then removed with the container holding member 96 from the carriage 93 and filled with a liquid having a predetermined viscosity. Thereafter, the container 98 is mounted in the container holding member 96 and connected to the carriage 93 by placing the pin 97 into the opening 94 in the carriage 93. The plunger 101 will, at this time, be extended from the upper end of the container 98. The cam 104 is adjusted so that the cam surface 106 is at the desired angle relative to the longitudinal axis of the guide rails 91 and 92. As a result, when the carriage 93 moves from its rightmost position to its left position, the plunger will be depressed into the container to effect an ejection of a precisely prescribed amount of the liquid from the nozzle 99.

After the container 98 has been properly positioned with its container holding member onto the carriage 93, the operator may then close the START switch. A closing of the START switch will effect an energization of the control relay CR1 to cause all of the relay contacts thereon to change their illustrated condition in FIG. 8. For example, the relay contacts CR1-1, CR1-3, CR1-4 and CR1-5 will become closed, whereas the remaining contact CR1-2 will become open. A closing of the contact CR1-3 will permit an energization of the control relay CR2 to cause the contacts CR2-1 and CR2-2 to become closed and the contact CR2-3 to open. The contact CR2-1 will effect a locking on of the START switch to hold the control relay CR2 in the energized condition. Simultaneously therewith, a time cycle light will be energized through the now closed contacts CR1-4 and CR2-2. The now open contact CR2-3 will de-energize the solenoid 125. Simultaneously therewith, the air compressor drive motor M1 will be energized to cause air to be supplied to the accumulator tank in the housing 17 and the solenoid 88 (see also FIG. 7) on the valve 86 will be energized to exhaust the pressure end of the power cylinder 83 to cause the spring in the power cylinder to retract the piston rod to the right. Thus, the weights 21 will apply a torque to the shaft 33 and cause the flat plate 38 to move into engagement with the roller 58 with a precisely controlled amount of force. It is important that the flat plate 38 apply a uniform force to the roller 58 across the width thereof so that the strip P clamped therebetween will not be crushed at one location along the width caused by the application of too much pressure and have too little pressure applied thereto at other locations along the width. If the strip P is not uniformly thick across the width thereof, an auxiliary support structure for the plate 38 can be used and is described in detail below. A time delay circuit 119 will be energized simultaneously with the solenoid 88 and a short time later a solenoid 121 will be energized on the drive motor 102 to cause the carriage 93 to move leftwardly from the broken line position of FIG. 5 to the solid line position thereof. Simultaneously with this leftward movement, the plunger 101 will engage the cam surface 106 and the plunger will be urged downwardly into the container 98 to eject the precise amount of liquid in the container into the V-like reservoir defined by the upper surface of the paper P on the roller 58 and the adjacent surface of the flat plate 38. Upon the carriage 98 reaching its leftmost position, the proximity switch LS-1 will become closed and this will effect an energization of the control relay CR3 through the closed contact CR1-5. An energizing of the control relay CR3 will effect a closing of the contacts CR3-1, CR3-2 and CR3-3. A closing of the contact CR3-1 will effect a locking on of the proximity switch LS-1. Simultaneously therewith, a closing of the contact CR3-2 will effect an energizing of the time delay circuit 122. A predefined interval of time later, a solenoid 123 will become energized to effect an air supply to the conduit 43 so that air will be supplied to the air nozzles 44 and 46. Since the liquid has been deposited into the aforementioned reservoir, the air output from the nozzles 44 and 46 will set up an air dam to keep the liquid deposited in the reservoir between the outlet openings of the nozzles 44 and 46. Simultaneously therewith, a further time delay circuit 124 will become energized so that at a predefined time interval later, the drive motor 63 will be energized to effect a driving of the cylindrical roller 58. The timing device 116 will also be simultaneously energized with the drive motor 63. Thus, the time interval is started at this particular point in the cycle of operation.

A closing of the relay contacts CR3-3 will prepare the circuit containing the light source 111 and the phototube 113 for activation of the control relay CR4. However, since the liquid has been deposited into the aforementioned reservoir, the light beam will not strike the phototube 113 because it will be blocked by the liquid in the reservoir and, therefore, the control relay CR4 will not become energized at this particular moment in time.

The paper P now moves through the line of contact between the roller 58 and the flat plate 38 down into the receiving tray 52. During this movement, the liquid will remain in the reservoir due to the predefined amount of uniformly applied pressure that the flat plate 38 applies against the roller surface 58. However, since the paper has a certain unknown smoothness and porosity characteristic, liquid will be absorbed into the paper strip as it passes through the nip. The air dam defined by the air blowing into the reservoir will keep the liquid precisely defined between the nozzles 44 and 46. Once the liquid has been fully absorbed into the paper strip, the light beam along the path 112 will make contact with the phototube 113 and effect a closing of the circuit to effect an energization of the control relay CR4. The contacts CR4-1 and CR4-2 will promptly become open to discontinue the energization of the solenoid 121 on the drive motor 102 and to promptly terminate the operation of the motor 63 and de-energize the timer 116. Thus, the timer 116 will indicate the total interval of time that it took to effect an absorption of the liquid into the paper strip.

The operator can now take the information that is available to him, namely, the viscosity of the liquid, the speed of movement of the movable surface, in this instance, the number of revolutions per minute of the cylindrical roller 58, the interval of time indicated on the timer 116 and the amount of pressure applied by the flat plate 38 onto the roller 58 as the paper strip P passes therebetween to determine a coefficient C based upon a solution to the following equation:

$$C = (\text{Viscosity}/\text{RPM}) \times \text{time} \times \text{pressure}$$

If the coefficient that is produced by placing the known data into the aforementioned formula is higher or lower than desired, this will immediately indicate to the operator as to whether a particular strip of paper has the desired smoothness and porosity characteristics to facilitate a coating thereof with a suitable material to thereby prevent a smearing of this material onto the next adjacent sheet in a stack of sheets. Since paper initially comes in large size rolls, a sample strip of paper can be removed from various segments of the strip so that the consistency of the paper on the roll can be periodically checked. As a result of our development, we have provided a solution to the problem of determining, with the required degree of accuracy, an answer to the problem of determining the characteristic of a particular strip of material as to its smoothness and porosity.

As indicated above, it can occur that the porous strip of material can have a nonuniform thickness across the width thereof, namely a maximum variance of 0.003 inches over a four-inch wide strip. Any variance exceeding the maximum allowable amount is generally unacceptable to the paper industry, especially in instances where the paper is to be coated as specified above. It is to be understood that other rollers having other deformation characteristics can be used to achieve the same objective. In this instance, the structure disclosed hereinabove for urging the plate 38 into engagement with the material will, if the strip is thicker on one edge than at the other, crush the thicker edge or will cause the plate 38 to lift away from the material at the thinner edge. The ability of the roller to be deformed will maintain the thinner edge in engagement with the plate 38 up to a paper thickness exceeding 0.003 inches. Once the plate lifts away from the strip, the liquid in the reservoir will quickly flow past the line of engagement between the plate 38 and the roller 58 to bring an abrupt halt to the test due to the fact that the photocell circuit will deactivate the drive for the roller 58.

ALTERNATE CONSTRUCTION (FIGS. 9 TO 12)

The support structure of the alternate construction of FIGS. 9 to 12 is identical to that which has been described above except for a modified construction of the mounting bracket 34A. Accordingly, the same reference numerals that have been utilized above will be used in the description of the alternate construction in FIGS. 9 to 12 and those components which are different will have new reference numerals set forth below.

Figure 9:
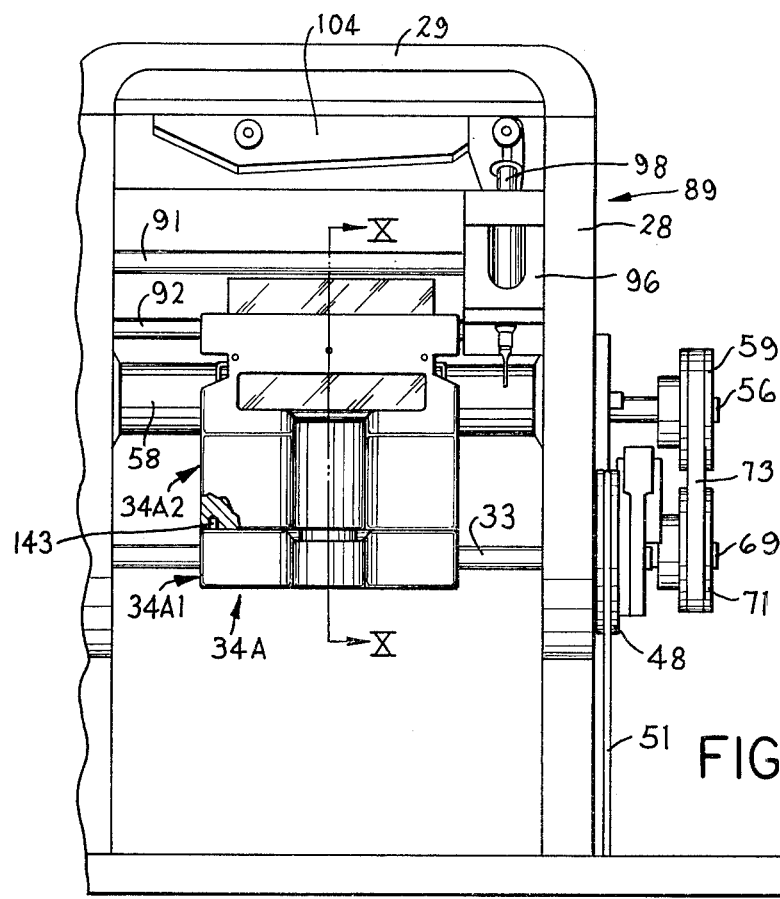
FIG. 9 is a view similar to FIG. 3 of a modified flat plate support structure.

Referring to FIG. 9, the mounting bracket 34A is secured to the shaft 33 by any convenient means, as by setscrews not illustrated. The mounting bracket 34A has a flat surface 131 facing the roller 58 and appropriate opposed, flat guide surfaces 132 for holding the lateral edges of a flat plate 133 fixedly oriented with respect to the mounting bracket 34A. A recess 134 is provided in the mounting bracket 34A on a side thereof facing the roller 58. A pair of axles 136 and 137 extends laterally of the recess 134 and in parallel relationship to each other and to the guide surfaces 132. In addition, the axles 136 and 137 are resiliently biassed to a centered position in an appropriate opening in the wall of the mounting bracket 34A and are capable of movement toward and away from the plane defined by the flat guide surface 132. The structure for facilitating this centering function is well known in the art and is, therefore, not illustrated. The axles 136 and 137 are each covered by a cylindrical roller 138 and 139, respectively. The rollers 138 and 139 engage the surface of the flat plate 133 remote from the roller 58 to resiliently urge the flat plate 133 into engagement with the flat guide surface 132. These rollers are similar to the roller 41 described above in the preceding embodiment.

An air supply manifold 42 is provided on the modified mounting bracket 34A in the same manner as in the embodiment of FIGS. 1 to 8 described above. Air is supplied to the manifold 42 through a conduit 43.

Figure 11:
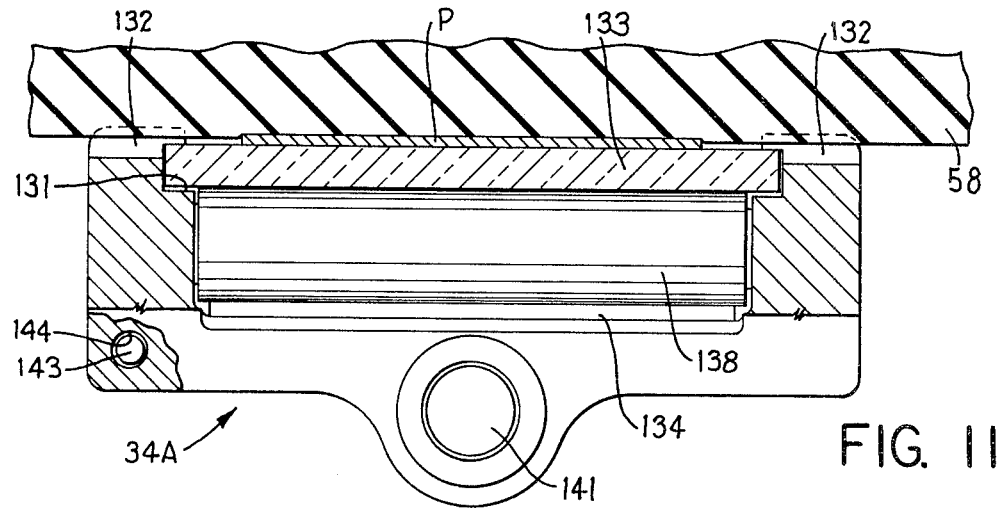
FIG. 11 is a sectional view taken along the line XI—XI of FIG. 10.
Figure 12:
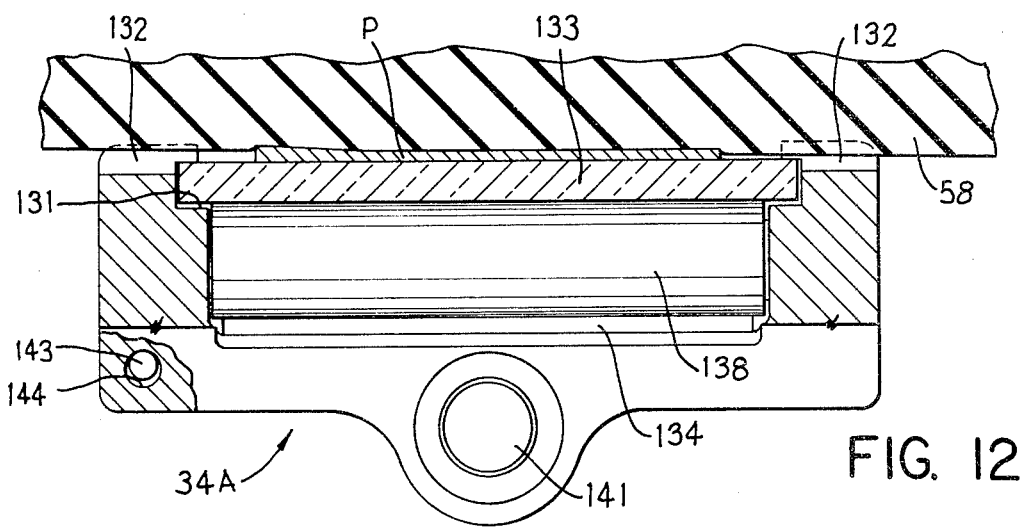
FIG. 12 is a view similar to FIG. 11 but having a nonuniformly thick strip of material between the flat plate and the roller.
Figure 13:
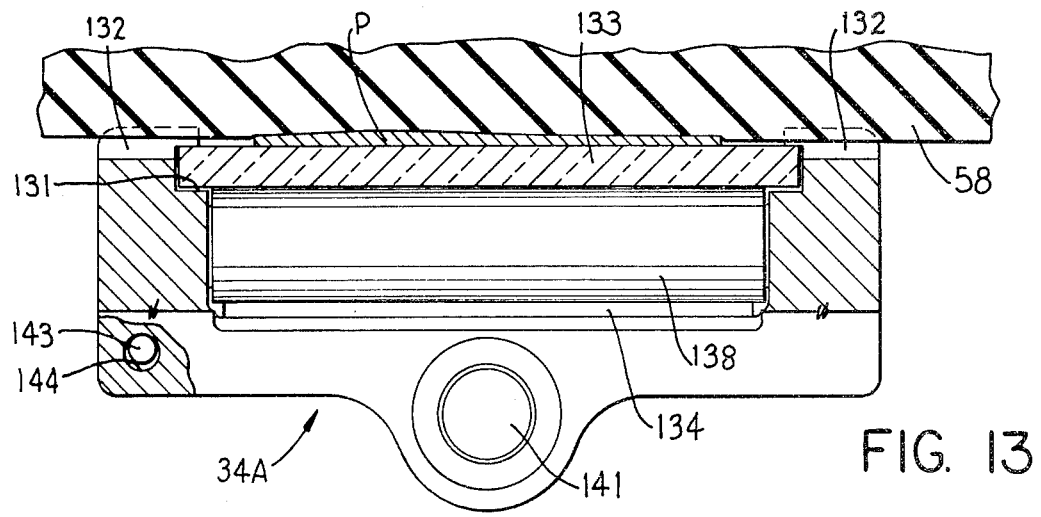
FIG. 13 is a view similar to FIG. 12.

In this particular embodiment, the modified mounting bracket 34A is composed of two parts, namely, a lower part 34A1 and an upper part 34A2. The lower part is fixedly secured to the shaft 33 as aforesaid. A shaft 141 is secured to the lower part 34A1 and extends upwardly therefrom with the axis thereof extending generally parallel to the plane of the flat guide surface 132. The upper part 34A2 has a cylindrical opening 142 therein adapted to receive the shaft 141 therein. Appropriate axially spaced bearings 143 and 144 are housed on the upper part 34A2 and serve to render the upper part 34A2 rotatable with respect to the shaft 141. In addition, the upper part 34A2 can be slid axially along the shaft 141 so that it can be removed therefrom. A guide pin 143 (FIGS. 11 and 12) extends upwardly from the lower part 34A1 and is received in a recess 144 having a diameter larger than the diameter of the pin 143 so that the upper part 34A2 can rotate about the axis of the shaft 141 through a limited range limited by the amount that the recess is larger than the diameter of the pin 143 received therein. This rotary movement will enable the flat plate 133 to compensate for nonuniform thicknesses in the porous strip which is to be tested. For example, FIG. 11 illustrates a porous strip P having a uniform thickness positioned between the flat plate 133 and the roller 58. FIG. 12 illustrates a porous strip P having a nonuniform thickness across the width thereof. It will be noted in this particular view that the left edge of the strip P is thicker than is the right edge. The amount that the pin 143 moves relative to the limit defined by the recess 144 is clearly depicted by a comparison of such structure in FIGS. 11 and 12. If the roller 58 has the deformation characteristics specified above, a wandering of the thickest portion of the strip to the middle of the strip width will prevent the plate 131 from lifting away from the roller 58 at the lateral edges thereof, such as shown in FIG. 13.

Figure 10:
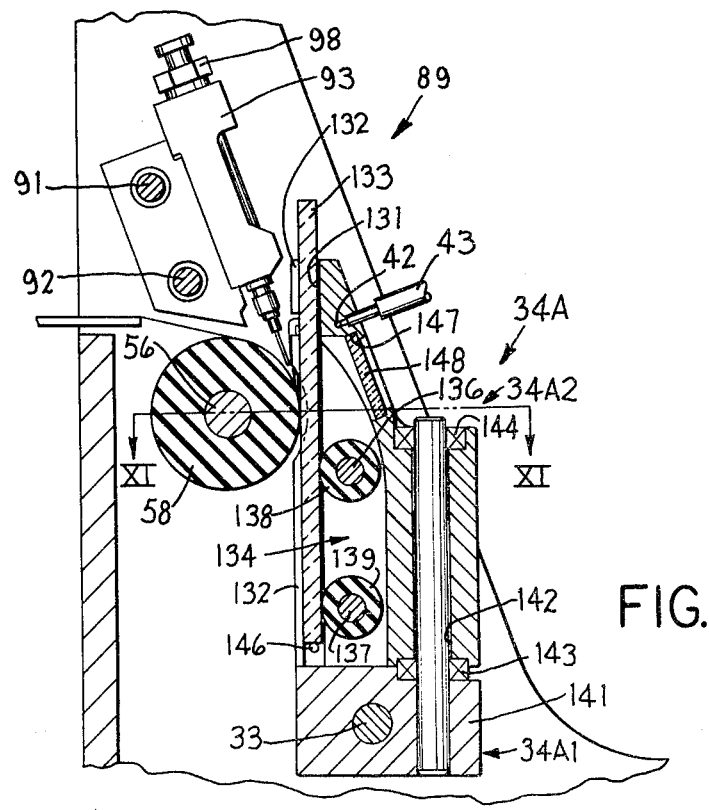
FIG. 10 is a sectional view taken along the line X—X of FIG. 9.

It will be noted in FIG. 10 that the glass plate 133 rests on a pair of laterally spaced pins 146. The pins offer the least amount of frictional resistance should the plate 133 shift due to a yielding of the spring loaded axles 136 and 137.

A window opening 147 is provided in a wall of the recess 134 to facilitate a viewing of the reservoir between the glass plate 131 and the roller 58. A glass piece 148 can, if desired, be placed in the window opening.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A smoothness absorbency tester for testing the smoothness and absorption characteristic of an elongated porous strip of material, comprising:
   frame means;
   movable surface means on said frame means and drive means therefor, said surface means being adapted to support said strip of porous material to be tested;
   blade means on said frame means and support means supporting at least one of said blade means and said movable surface means for movement toward and away from the other thereof;
   first means for urging said blade means and said movable surface means into engagement with each other with a predefined amount of force to define an upwardly opening reservoir, said strip of material being driven with said movable surface means past said blade means;
   liquid dispensing means for dispensing a liquid of a predetermined viscosity into said reservoir so that the said liquid contacts said strip of material, said blade means preventing a run off of said liquid in the direction of movement of said strip of material and thereby holding said liquid in said reservoir to be absorbed by said strip of material;
   sensing means for detecting the presence or absence of a liquid in said reservoir, said sensing means including second means for producing a signal in response to the absence of liquid in said reservoir; and
   timing means operatively interconnected to said liquid dispensing means and said sensing means, and automatically responsive to said signal, for timing an interval of time between the introduction of liquid into said reservoir and the indication of the absence of liquid therein.

2. The smoothness absorbency tester according to claim 1, wherein said surface means includes a cylindrical roller and wherein said blade means includes a planar plate engaging said roller uniformly along the length thereof and forming a tangent to the surface of said roller.

3. The smoothness absorbency tester according to claim 2, wherein said planar plate includes pivot means for pivotally securing said planar plate to said frame means and is movable toward and away from the surface of said roller about the pivot axis of said pivot means.

4. The smoothness absorbency tester according to claim 3, wherein said planar plate includes pivot means pivotally supporting said planar plate for movement about a pivot axis extending parallel to the plane of said planar plate.

5. The smoothness absorbency tester according to claim 3, wherein said first means includes a weight of predetermined magnitude suspended from said planar plate at a radial distance from said pivot axis to effect an urging of said planar plate into engagement with said roller with said predetermined amount of force.

6. The smoothness absorbency tester according to claim 1, wherein said liquid dispensing means includes a carriage means supported for movement transversely of the direction of travel of said surface means and above said reservoir, a liquid dispenser container mounted on said carriage means and movable therewith, said container having an outlet located over said reservoir and ejection means for effecting an ejection of said liquid from said container in response to a movement of said carriage means transversely of said surface means.

7. The smoothness absorbency tester according to claim 6, wherein said container is a hollow cylinder having a plunger reciprocally movable in said hollow cylinder, said plunger being moved to effect an ejection of liquid from said container in response to said movement of said carriage means.

8. The smoothness absorbency tester according to claim 7, wherein said frame means has a track and a cam surface extending coextensively with said track, said carriage means being movably mounted on said track, said cam surface being inclined relative to said truck so that one end of said cam surface is closer to said track than the other end, said plunger slidingly engaging said cam surface and being urged into said container in response to said movement of said carriage means.

9. The smoothness absorbency tester according to claim 8, wherein said frame means includes adjustment means for adjusting the angle of inclination of said cam surface relative to said track.

10. The smoothness absorbency tester according to claim 1, including adjustment means for adjusting the speed of movement of said surface means.

11. The smoothness absorbency tester according to claim 1, wherein said blade means includes a plate of finite width engaging said movable surface means and nozzle means spaced inwardly on opposite lateral edges of said plate and said strip of material, said nozzle means having a pressurized gas supply connected thereto so that said gas will be directed into said reservoir at the lateral sides thereof to define a pair of spaced air dams keeping said liquid from running out of said reservoir through the lateral edges thereof.

12. The smoothness absorbency tester according to claim 11, wherein said means comprises a light source and a photosensor having a sight line operatively related to said light source, said light source and said photosensor being positioned on opposite sides of said reservoir and aligned so that said sight line extends generally parallel to the line of intersection between said plate and said surface means and through said pair of air dams, said sight line being obstructed by the presence of liquid in said reservoir.

13. The smoothness absorbency tester according to claim 1, including means responsive to said signal indicating of the absence of a liquid in said reservoir to effect a stoppage of the movement of said surface means and said strip of material supported thereon.

14. The smoothness absorbency tester according to claim 13, wherein said timing means includes circuit means for timing said interval of time that said drive means moves said surface means.

15. The smoothness absorbency tester according to claim 13, wherein said timing means includes variable time delay circuit means for varying the point in time that said time interval is to begin.

16. A smoothness absorbency tester for testing the smoothness and absorption characteristic of an elongated porous strip of material, comprising:
frame means;
movable surface means on said frame means and drive means therefor, said surface means being adapted to support said strip of porous material to be tested;
blade means on said frame means and support means supporting at least one of said blade means and said movable surface means for movement toward and away from the other thereof;
first means for urging said blade means and said movable surface means into engagement with each other with a predefined amount of force to define an upwardly opening reservoir, said strip of material being driven with said movable surface means past said blade means;
liquid dispensing means for dispensing a liquid of a predetermined viscosity into said reservoir so that said liquid contacts said strip of material, said blade means preventing a run off of said liquid in the direction of movement of said strip of material and thereby holding said liquid in said reservoir to be absorbed by said strip of material;
nozzle means spaced inwardly on opposite lateral edges of said blade means and said strip of material, said nozzle means having a pressurized gas supply connected thereto so that said gas will be directed into said reservoir at the lateral sides thereof to define a pair of spaced air dams keeping said liquid from running out of said reservoir through the lateral edges thereof;
a light source and a photosensor having a sight line operatively related to said light source, said light source and said photosensor being positioned on opposite sides of said reservoir and aligned so that said sight line extends generally parallel to the line of intersection between said blade means and said surface means and through said pair of air dams, said sight line being obstructed by the presence of liquid in said reservoir; and
timing means operatively interconnected in circuit with said photosensor and said liquid dispensing means, and automatically responsive to the detection of light by said photosensor from said light source following the introduction of liquid in said reservoir, for indicating the total lapsed time between the introduction of liquid into said reservoir and the detection of light by said photosensor.

* * * * *

UNITED STATES PATENT AND TRADEMARK OFFICE
CERTIFICATE OF CORRECTION

PATENT NO. : 4 259 862
DATED : April 7, 1981
INVENTOR(S) : Lloyd D. Sheaks and W. Howard Drew It is certified that error appears in the above—identified patent and that said Letters Patent is hereby corrected as shown below:

Col. 5, line 20; change "aforesiad" to ---aforesaid---.

Col. 13, line 27; after "said" insert ---second---.

Col. 13, line 39; after "including" insert ---third---.

after "signal" insert ---for---.

line 40; delete "of" (first occurrence).

Signed and Sealed this

Twenty-fifth Day of August 1981

[SEAL]

Attest:

GERALD J. MOSSINGHOFF

Attesting Officer     Commissioner of Patents and Trademarks